United States Patent [19]
Wakatake

[11] Patent Number: 5,380,488
[45] Date of Patent: Jan. 10, 1995

[54] CONTAINER FEEDING SYSTEM
[75] Inventor: Koichi Wakatake, Tokyo, Japan
[73] Assignee: Kabushiki Kaisha Nittec, Tokyo, Japan
[21] Appl. No.: 925,676
[22] Filed: Aug. 7, 1992
[30] Foreign Application Priority Data
  Mar. 19, 1992 [JP] Japan .................. 4-112042
[51] Int. Cl.6 .......................... G01N 21/00
[52] U.S. Cl. .......................... 422/65; 422/63; 422/67; 422/68.1; 436/43; 436/47; 414/331
[58] Field of Search .......... 422/63, 65, 67, 68.1; 414/331, 222; 436/43, 47

[56] References Cited
U.S. PATENT DOCUMENTS

| | | | |
|---|---|---|---|
| 4,054,415 | 10/1977 | Seligson et al. | 422/64 X |
| 4,058,367 | 11/1977 | Gilford | 422/67 |
| 4,363,782 | 12/1982 | Yamashita | 422/65 |
| 4,710,352 | 12/1987 | Slater et al. | 422/63 |
| 4,861,553 | 8/1989 | Mawhirt et al. | 422/65 |
| 4,861,554 | 8/1989 | Sakuma | 422/65 |
| 4,956,148 | 9/1990 | Grandone | 422/64 |
| 5,008,082 | 4/1991 | Shaw | 422/65 |
| 5,084,242 | 1/1992 | Sakuma et al. | 422/100 |
| 5,096,670 | 3/1992 | Harris et al. | 422/63 |
| 5,104,621 | 4/1992 | Pfost et al. | 422/67 |
| 5,122,342 | 6/1992 | McCulloch et al. | 422/65 |
| 5,209,903 | 5/1993 | Kanamori et al. | 422/65 |

Primary Examiner—James C. Housel
Assistant Examiner—Harold Y. Pyon
Attorney, Agent, or Firm—Lowe, Price, LeBlanc & Becker

[57] ABSTRACT

A container feeding system is disclosed, which includes a feed stocker for stocking racks holding containers, one or more sampling feeders connected to the downstream side of the feed stocker, and one or more analyzers for withdrawing samples from containers which are moved to sampling positions in an interlocked relation to the sampling feeder or feeders. One or more coupling feeders are connected to the respective downstream sides of the sampling feeder or feeders, and a treated container stocker is connected to the most downstream side of the coupling feeder or feeders. The individual components are provided as respective units. The number of sampling feeders and coupling feeders connected thereto can be increased or reduced, and in correspondence therewith so can the number of analyzers disposed along a rack feeding line. The rack feeding path can thus be readily increased and reduced, as desired, to meet the scale of the delivery side. Likewise, the control mechanism for controlling the feeding of containers with selective priority is also greatly simplified.

18 Claims, 3 Drawing Sheets

_CONTAINER FEEDING SYSTEM_

FIELD OF THE INVENTION

This invention relates to container feeding systems suited for the feeding of blood containers such as blood extraction tubes and, more particularly, to container feeding systems which permit a rack feeding path to be readily increased or reduced to meet the scale of the delivery side and also permit great simplification of a control mechanism for controlling the feeding of racks with priority.

BACKGROUND OF THE INVENTION

There are well-known container feeding systems for feeding containers such as blood extraction tubes held by racks along a belt conveyer line to predetermined analyzers for biochemical or immunological analysis.

In such prior art container feeding systems, container feeding lines and control systems are assembled as fixed components for delivery according to the scale of facilities to which the container feeding systems are delivered. In other words, container feeding systems of the same version can be delivered only to facilities of the same scale. This means that the versatility of the systems is very poor. In addition, since the systems are special order products, their cost is high.

In another aspect, some of the prior art container feeding systems, in which a plurality of analyzers are disposed one after another along a container feeding line, are adapted such that containers are fed with priority to analyzers ready to receive containers for analysis, In such a case, however, a single computer is used to grasp the status of analyzing in all the analyzers and controls the whole container feeding line according to the grasped information. Therefore, this kind of control is extremely complicated, thus leading to high cost.

SUMMARY OF THE INVENTION

A principal object of the invention, is to provide a container feeding system which permits ready increase or reduction of a rack feeding path to match the scale of a delivery side and also permits great simplification of a control mechanism for controlling the feeding of containers with priority.

Another object of the invention is to provide a container feeding system which permits improved of the versatility.

Yet another object of the invention is to provide a container feeding system which permits simplification of its control system as well as permitting great improvement of the versatility.

To attain the above objects according to a preferred embodiment of the invention, there is provided a container feeding system, which comprises: a feed stocker for stocking a plurality of racks holding containers, a rack feeding line along which racks fed out from the feed stockers are moved, and a plurality of analyzers disposed one after another along the rack feeding line, the analyzers being controlled such as to independently detect the status of feeding of racks along the rack feeding line and request upstream side analyzers to feed racks according to the detected status of feeding of racks.

According to another aspect of the invention, there is provided a container feeding system, which comprises: a feed stocker for stocking racks holding containers, one or more sampling feeders connected to the downstream side of the feed stockers, one or more analyzers for withdrawing samples from containers having reached sampling positions in an interlocked relation to the sampling feeders, one or more coupling feeders connected to the downstream side of the sampling feeder or feeders, and a treated container stocker connected to the downstream side of the coupling feeder or feeders, the individual components being provided as respective units, the number of the sampling feeder or feeders and the number of the coupling feeder or feeders being variable in correspondence to the number of analyzers disposed one after another along a rack feeding line.

According to yet another aspect of the invention, there is provided a container feeding system, which comprises: a feed stocker for stocking racks holding containers, one or more sampling feeders connected to the downstream side of the feed stocker, a plurality of analyzers for withdrawing samples from containers having reached sampling positions in an interlocked relation to the sampling feeder or feeders, one or more coupling feeders connected to the downstream side of the sampling feeder or feeders, and a treated container stocker connected to the downstream side of the coupling feeder or feeders, the individual components being provided as respective units, the analyzers being controlled such as to independently detect the status of feeding racks in the corresponding sampling feeder or feeders and request upstream side analyzer or analyzers to feed racks in accordance with the detected status of feeding racks.

BRIEF DESCRIPTION OF THE DRAWINGS

The above and other objects, features and advantages of the invention will become more apparent from the following description read with reference to the accompanying drawings, in which.

DETAILED DESCRIPTION OF THE PREFERRED EMBODIMENT

Figure 1:
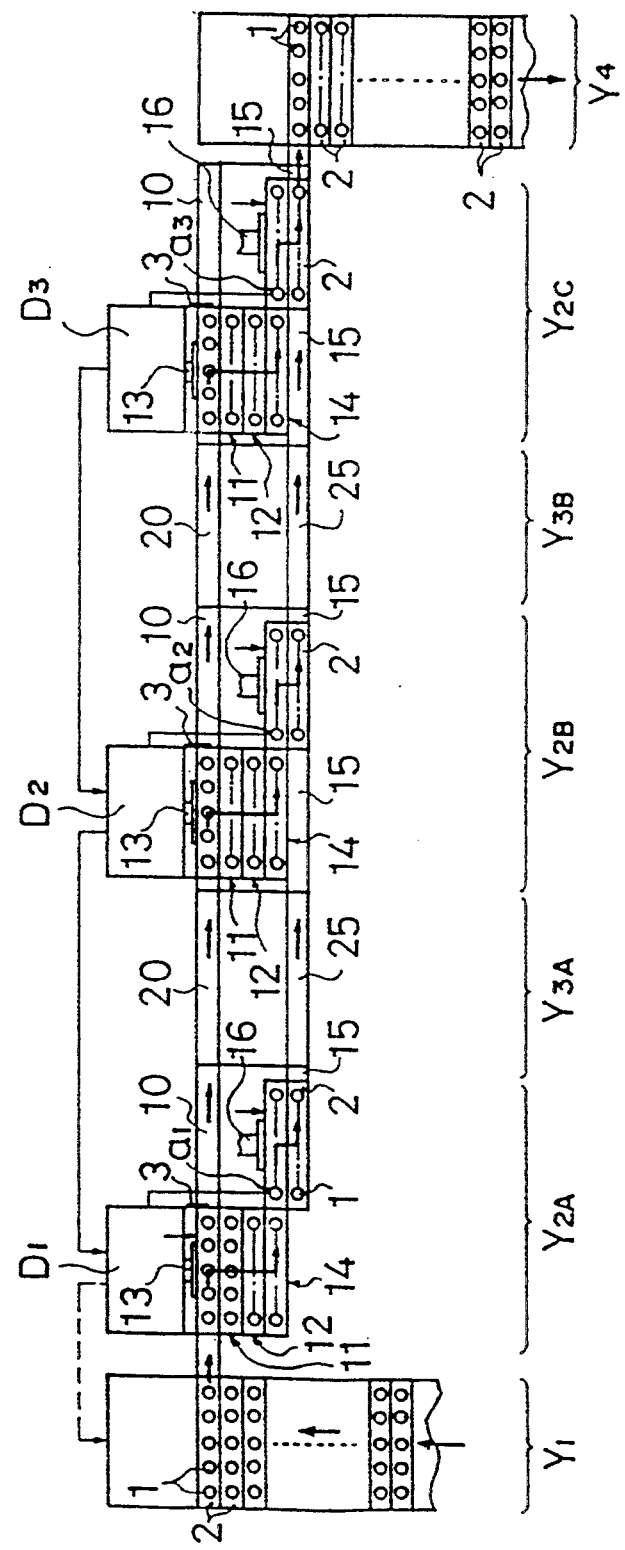
FIG. 1 is a schematic plan view showing a preferred embodiment of the container feeding system, which includes two coupling feeders, according to the invention.
Figure 2:
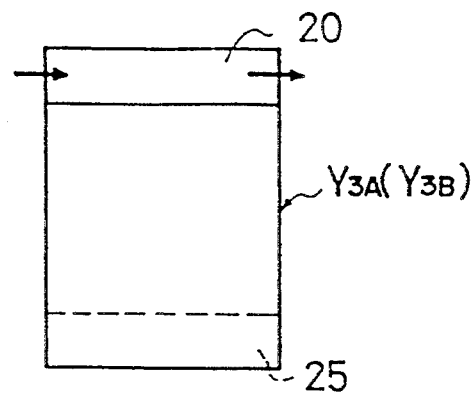
FIG. 2 is a fragmentary schematic plan view showing a different example of a coupling feeder of the container feeding system.

FIG. 1 shows a preferred embodiment of the container system according to the invention. The system comprises a feed stocker Y1, three sampling feeders Y2A–Y2C, three analyzers D1 to D3, two coupling feeders Y3A and Y3B and a treated container stocker Y4. These components are constructed as respective units. The feed stocker Y1 stocks a plurality of racks 2 holding containers 1 such as blood extraction tubes. The sampling feeders Y2A–Y2C have the same construction and are connected to the downstream side of the feed stocker Y1. The analyzers D1 to D3 withdraw samples from container 1 arriving at sampling positions al to a3 in an interlocked relation to the associated sampling feeders Y2A-Y2C. The coupling feeders Y3A and Y3B are connected to the downstream side of the respective sampling feeders Y2A and Y2B. The treated container stocker Y4 is connected to the downstream side of the coupling feeders Y3A and Y3B.

The racks 2 have a free size structure such that they can rigidly hold containers of various sizes. They have magnets (not shown) which provide weak magnetic forces. The rack 2 may hold a desired number of containers 1. The magnetic force of each magnet buried in the rack bottom is preferably small so as to permit the rack 2 to slide over the rack feeding line when the feeding of the track is stopped by a rack stopper 3.

While in this embodiment the rack 2 is adapted to hold a plurality of upright containers 1, it may be constructed as well to hold only a single container 1.

Each container 1 held by the rack 2 has its surface provided with information concerning the sample contained in The information is provided in the form of, for instance, a bar code, and it is automatically read out by bar code readers (not shown) provided in the vicinity of the sampling positions a1 to a3 of the sampling feeders Y2A to Y2C, the read-out information being automatically fed to controllers in the analyzers D1–D3.

The feed stocker Y1 is constructed such as to stock a plurality of racks 2 and feed the stocked racks 2 one by one to a rack feeding line to be described later. The rack feeding mechanism in the feed stocker Y1 may suitably use a well-known intermittent feeding mechanism such as an actuator or a belt conveyer, and it is not described in detail.

The sampling feeders Y2A-Y2C each include a rack feeding line 10, a waiting line 11, an emergency line 12, an urging device 13, a sampling line 14, a rack recovery line 15, a feeder (not shown), a pipette assembly (not shown), an urging device 16 and a rack feeder (not shown). The most upstream rack feeding line 10 (the one shown most to the left in FIG. 1) has its upstream end connected directly to the outlet of the feed stocker Y1. The next rack feeding line 10 has its upstream end connected to the downstream end 20 of the upstream side coupling feeder Y3A. The next rack feeding line 10 (the one most to the right in FIG. 1) has its upstream end connected to the downstream end of the rack feeding line 20 of the downstream side coupling feeder Y3B. The downstream end of the first rack feeding line 10 is connected directly to the upstream end 20 of coupling feeder Y3A, and the downstream end of the next rack feeding line 10 is connected directly to the upstream end 20 of coupling feeder Y3B. The provision of two coupling feeders Y3A and Y3B is only exemplary. The emergency line 12 extends parallel to the waiting line 11. The urging device 13 serves to urge a rack 2 on the rack feeding line 10 to the waiting line 11 or the emergency line 12. The sampling line 14 extends straight on the downstream side of the emergency line 12. The rack recovery line 15 extends parallel to the sampling line 14. The feeder (not shown) comprises a belt conveyer or the like for intermittently feeding a rack 2 on the emergency line 12 to the sampling line 14.

The pipette device serves to withdraw a predetermined amount of sample from each container 1 held by each rack 2 fed intermittently by the feeder and distributes the withdrawn sample to other containers (not shown) in the associated analyzers D1, D2 or D3.

The urging device 16 serves to urge a rack 2 holding containers 1, for all of which the sampling operation has been ended, from the sampling line 14 to the rack recovery line 15. The rack feeder (not shown) comprises a belt conveyer or the like for feeding each rack 2 on the rack recovery line 15 to the downstream side.

When checking an emergency sample, an emergency sample rack (not shown) held by the emergency line 12 is brought into the sampling line 14, by an emergency interruption before racks being fed in routine sequence. In the illustrated embodiment, the emergency line 12 is disposed parallel to the waiting line 11. However, it is possible to dispose the emergency line 12, waiting line 11 and sampling line 14 in series. In this case, an emergency rack which has been brought from the emergency line 12 into the waiting line 11 is fed straight from the waiting line 11 to the sampling line 14.

The sampling withdrawal, i.e., the sampling operation, is performed by a well-known pipette mechanism at each of the sampling positions a1 to a3 on the sampling lines 14 of the sampling feeders Y2A to Y2C. Prior to this sampling operation, a vacuum breaking (i.e., air purging) operation and an agitating operation are on the containers.

The coupling feeders Y3A and Y3B each have rack feeding and recovery lines 20 and 25 connected to the respective rack feeding and recovery lines 10 and 15 of the immediately upstream one of the sampling feeders Y2A and Y2B. These lines 20 and 25 serve to feed racks 2 one by one to the downstream side with rack feeders (not shown) such as belt conveyers.

Where the coupling feeder Y3A or Y3B is coupled to the treated container stocker Y4, either one of the rack feeding and recovery lines 20 and 25 may be provided in correspondence to the use.

Figure 3:
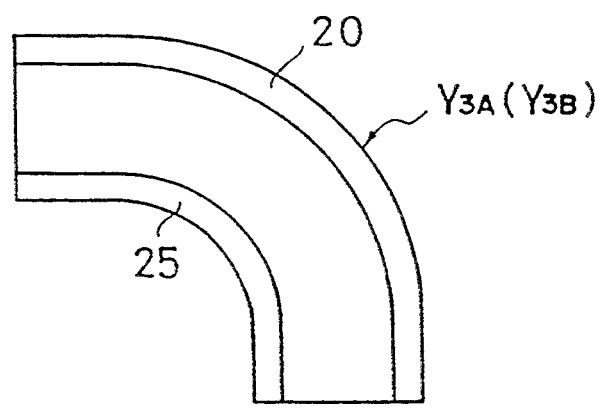
FIG. 3 is a fragmentary schematic plan view showing a further example of the coupling feeder.

Further, the rack feeding and recovery lines 20 and 25 of the coupling feeder Y3A or Y3B may be curved gently into an L-shaped form in plan view as shown in FIG. 3. Of course, these lines may be bent or curved into various other shapes as well, for instance meandering and channel-like shapes, to conform to the shapes of available installation space. Further, it is possible to provide an L-shaped line and provide a direction switch like a locomotive direction switch at the corner.

Figure 4:
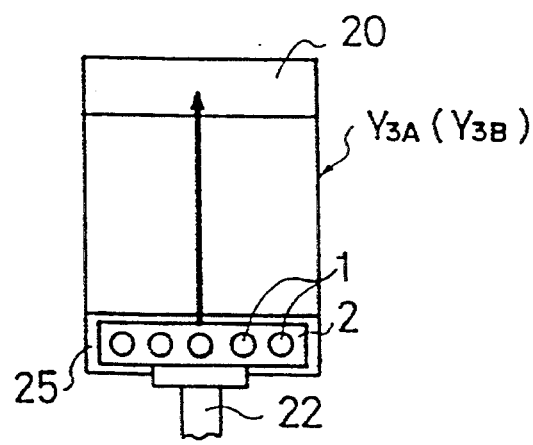
FIG. 4 is a fragmentary schematic plan view showing a further example of the coupling feeder.
Figure 5:
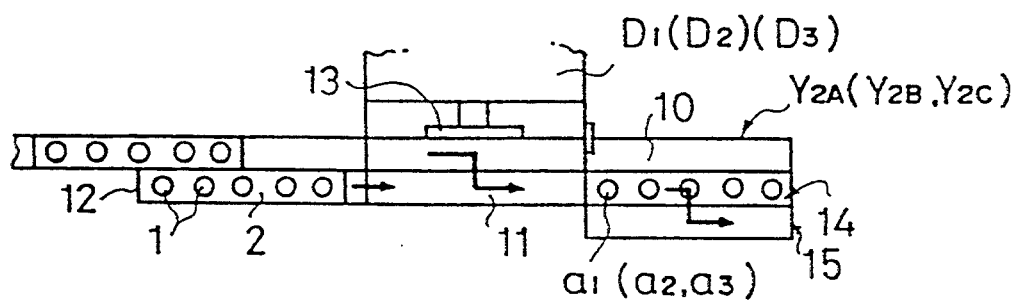
FIG. 5 is a fragmentary schematic plan view showing a different example of feeding line in the container feeding system.

Further, where the analyzers D1 to D3 are adapted to carry out different items of analysis, each rack 2 having been fed to the rack recovery line 25 in the coupling feeder Y3A or Y3B has to be returned to the rack feeding line 10 for a different analyzer. To this end, an urging device 22 provided to urge a rack 2 on the rack recovery line 25 to the rack feeding line 20, as shown in FIG. 4.

The treated container stocker Y4 has generally the same construction as the feed stocker Y1 except for that it stocks one by one the treated container racks which are brought to recovery line B after the sampling operation, hence is not described here in detail.

In the illustrated embodiment, per FIG. 1 the analyzers D1 to D3 are of the same type and carry out the same analysis, and they are constructed such that they can independently detect the status of feeding of containers 1 in the corresponding sampling feeders Y2A to Y2C.

More specifically, the individual analyzers D1 to D3 instantaneously monitor racks 2 on the individual lines of the sampling feeders Y2A to Y2C via sensors (not shown) disposed on the lines, and the controllers (i.e., CPUs) of the analyzers D1 to D3 are connected to one another such that each can request an upstream side analyzer to feed a rack to an analyzer, which can carry out sampling of containers 1 with the utmost priority.

For example, when racks 2 are present on all the lines of the sampling feeders Y2A and Y2B corresponding to the analyzers D1 and D2 while lines in the sampling feeder Y2C are ready to receive racks 2, the controller (CPU) of the analyzer D3 requests the controller (CPU) of the analyzer D2 to feed racks 2 with priority.

At this time, since racks 2 are present on all the lines of the sampling feeder Y2B, the controller (CPU) of the aalyzer D2 provides a command to the controller (CPU) of the analyzer D1 such that a rack 2 be fed through the rack feeding line 10 in the sampling feeder Y2B to the rack feeding line 10 of the sampling feeder Y2B, while at the same time requesting the controller (CPU) of the analyzer D1 to feed a rack 2 with priority.

Upon receipt of this request, at which time the racks 2 are present on all the lines in the sampling feeder Y2A, the controller (CPU) of the analyzer D1 provides a command to the controller (CPU) of the sampling feeder Y2A such that a rack 2 be fed through the rack feeding line 10 in the sampling feeder Y2B to the rack feeding line 10 in the sampling feeder Y2B.

Thus, racks 2 having been fed out from the feed stocker Y1 are fed via the rack feeding line 10 in the sampling feeder Y2A, rack feeding line 20 in the coupling feeder Y3A, rack feeding line 10 in the sampling feeder Y2B, rack feeding line 20 in the coupling feeder Y3B and rack feeding line 10 in the sampling feeder Y2C in the mentioned order.

Further, when racks 2 are present on lines in the sampling feeder Y2A corresponding to the analyzer D1 and lines in the sampling feeders Y2B and Y2C corresponding to the analyzers D2 and D3 are ready to receive racks 2, the controller (CPU) of the analyzer D3 first requests the controller (CPU) of the analyzer D2 to feed a rack 2 with priority.

At this time, since lines in the sampling feeder Y2B are ready to receive rack 2, the controller (CPU) of the analyzer D2 receives the request from the controller (CPU) of the analyzer D3 and requests the controller (CPU) of the analyzer D1 to feed a rack 2.

Upon receipt of this request, at which time racks 2 are present on all the lines in the sampling feeder Y2A, the controller (CPU) of the analyzer D1 provides a command to the controller (CPU) of the sampling feeder Y2A such that a rack 2 be fed through the rack feeding line 10 in the sampling feeder Y2A to the rack feeding line 10 in the sampling feeder Y2B.

Consequently, racks 2, having been fed out from the feed stocker Y1, are fed via the rack feeding line 10 in the sampling feeder Y2A, rack feeding line 20 in the coupling feeder Y3A and rack feeding line 10 in the sampling feeder Y2B.

When the lines in the sampling feeder Y2B become full, the feeding of racks 2 to the sampling feeder Y2C corresponding to the analyzer D3, is effected in accordance with the procedure as described above.

In this embodiment of the container feeding system, if the sampling feeder Y2A corresponding to the analyzer D1 is ready to receive racks 2, racks 2 are fed with priority to the rack feeding line 10 in the sampling feeder Y2A.

Thus, in this embodiment of the container feeding system a rack 2 fed out from the feed stocker Y1 is first fed to the rack feeding line 10 in the sampling feeder Y2A, and at this position the rack stopper 3 in the sampling feeder Y2A is operated to block the feeding of the rack 2 to the downstream side.

Then, the urging device 13 in the sampling feeder Y2A is operated to urge the rack 2, which has been held stationary on the rack feeding line 10 in the sampling feeder Y2A, to the waiting line 11. When the next rack 2 is fed in the same procedure to the waiting line 11, the rack 2 having been waiting in the waiting line 11 is fed to the emergency line 12. Each rack 2 fed to the emergency line 12 is fed intermittently to the sampling line 14 provided on the downstream side of the emergency line 12 for sample withdrawal by the pipette at the sampling position a1. Subsequently, the rack 2 is urged to the rack recovery line 15 by the urging device 16, and then it is fed via the rack recovery line 25 in the coupling feeder Y3A, rack recovery line 15 in the sampling feeder Y2B, rack recovery line 25 in the coupling feeder Y3B and rack recovery line 15 in the sampling feeder Y2C to the treated container stocker Y4.

When the lines in the sampling feeder Y2A are full of racks 2, succeeding racks 2 are fed via the rack feeding line 10 in the sampling feeder Y2A in a bypass line to the rack feeding line 10 in the sampling feeder Y2B. The procedure of feeding of racks 2 fed to the rack feeding line 10 in the sampling feeder Y2B is the same as in the sampling feeder Y2A, and therefore it is not described here.

Further, when the lines in the sampling feeders Y2A and Y2B, are full succeeding racks 2 are fed via the rack feeding lines 10 in the sampling feeders Y2A and Y2B, acting as bypass line, to the rack feeding line 10 of the sampling feeder Y2C. The procedure of feeding of racks 2 fed to the rack feeding line 10 in the smapling feeder Y2C is the same as in the case of the sampling feeders Y2A and Y2B, and therefore it is not described here.

The above-described procedures could result in a situation when racks 2 are present on all the lines in the sampling feeders Y2A and Y2B corresponding to the analyzers D1 and D2 while lines in the sampling feeder Y2C corresponding to the analyzer D3 are ready to receive racks 2, and also when racks 2 are present on lines in the sampling feeder Y2A corresponding to the analyzer D1 while the lines in the sampling feeders Y2B and Y2C are ready to receive racks 2. Under these circumstances the controller (CPU) of an analyzer in charge of a redundant rack feeding line can request the controller (CPU) of an upstream side analyzer to feed racks with priority as noted above, hence it is possible to obtain efficient feeding of racks. Besides, the controllers (CPUs) of the individual analyzers D1 to D3 need not detect the rack feed status of all the rack feeding lines. Thus, it is possible to greatly simplify the construction of the control system.

Further, as is obvious from the above described embodiment, with the container feeding system according to the invention the sampling feeders Y2A to Y2C and coupling feeders Y3A and Y3B connected thereto are provided as independent units to be suitably connected, in what may be called a "modular" manner, for assembling a system corresponding to the scale of the delivery side. Thus, it is possible to avoid high cost like those that would arise in forming a special order system. In addition, the versatility of the system, by selecting as many element as needed can be greatly improved.

In the above embodiment, three analyzers D1 to D3 for performing identical analysis are disposed one after another along a rack feeding line. However, this embodiment is by no means limitative. For example, it is possible to provide a plurality of analyzers for performing a first item of analysis and a plurality of other analyzers for performing a different item of analysis along a rack feeding line. In this case, a relay stocker (not shown) may be provided, which has the same construction as the feed stocker Y1 or the treated container stocker Y4, such that racks after sampling operation by the analyzers for one item of analysis are tentatively stocked in the relay stocker before being fed to the rack feeding line in the analyzers for the other item of analysis. In general, it is possible to select various variations to assemble the system.

As has been described in the foregoing, the container feeding system according to the invention permits the rack feeding path to be readily increased or reduced to meet the scale of the delivery side. In addition, the control mechanism for controlling the feeding of containers with priority can be greatly simplified, thus permitting great reduction in the cost such a system. Further, it is possible to obtain great improvement of the versatility of the system.

Although the invention has been described with respect to a specific embodiment for a complete and clear disclosure, the appended claims are not to be thus limited but are to be construed as embodying all modifications and alternetive constructions that may occur to one skilled in the art which fairly fall within the basic teaching herein set forth.

What is claimed is:

1. A container feeding system, formed of a cooperating set of components comprising:
   rack stocker means for stocking and feeding out a plurality of racks each holding a plurality of containers for containing respective samples;
   a rack feeding line cooperating with said rack stocker means, on and along which racks fed out from said rack stocker means are fed only in a downstream direction relative to said rack stocker means;
   a plurality of analyzers disposed sequentially along and adjacent to said rack feeding line;
   control means for controlling said components,
   said analyzers each being controlled by the control means to independently detect a status of said racks that are being fed along said rack feeding line and to request another of said analyzers which is located at an upstream location to feed racks according to the detected status of said racks;
   a rack recovery line disposed in parallel to said rack feeding line; and
   urging means for selectively urging each rack that has passed a selected one of said analyzers from said rack feeding line to said rack recovery line.

2. A container feeding system, formed of a cooperating set of components comprising:
   a rack feeding line;
   rack stocker means, for stocking and feeding out a plurality of racks, with each rack holding a plurality of containers for containing respective samples, on and along said feeding line in a downstream direction;
   at least one sampling feeder connected to a downstream side of said rack stocker means to receive said racks therefrom on and along said rack feeding line;
   a rack recovery line disposed in parallel to said rack feeding line;
   urging means for selectively urging each rack that has passed a selected one of said analyzers from said rack feeding line to said rack recovery line;
   at least one analyzer for withdrawing samples from containers which have reached a sampling position, disposed in an interlocked relation to said at least one sampling feeder;
   at least one coupling feeder connected to a downstream side of said at least one sampling feeder to enable controlled movement of racks therefrom; and
   a treated container stocker, connected to a downstream side of said at least one coupling feeder,
   said components being provided in selected numbers to operate in cooperation as respective cooperating units, wherein each unit comprises a sampling feeder, a coupling feeder, and an analyzer, the respective analyzers being disposed one after another along said rack feeding line for sampling said racks that are fed from said rack stocker means to said treated container stocker.

3. A container feeding system, formed of a cooperating set of components comprising:
   a rack feeding line;
   rack stocker means, for stocking and feeding out to said rack feeding line a plurality of racks each holding a plurality of containers for containing respective samples;
   at least one sampling feeder, connected to a downstream side of said rack stocker means to receive and move said racks therefrom on and along said rack feeding line only in a downstream direction;
   a plurality of analyzers, for withdrawing samples from containers which have reached predetermined sampling positions, respectively disposed in interlocked relation to said at least one sampling feeder;
   at least one coupling feeder, connected to a downstream side of said at least one sampling feeder to receive said racks therefrom on and along said rack feeding line;
   a rack recovery line disposed in parallel to said rack feeding line;
   urging means for selectively urging each rack that has passed a selected one of said analyzers from said rack feeding line to said rack recovery line;
   a treated container stocker, connected to a downstream side of said at least one coupling feeder to receive said racks therefrom on and along said rack feeding line; and
   control means for controlling said components,
   said components being provided in selected numbers so as to include a plurality of cooperating units, wherein each unit comprises a sampling feeder, a coupling feeder and an analyzer, each of said analyzers being controllable by the control means to independently detect a status of racks being fed in a corresponding one of said sampling feeders and to request a coupling feeder that is located relatively upstream thereof to feed additional racks in accordance with a detected status of feeding of said racks.

4. The container feeding system according to claim 1, wherein:
   stopper means for selectively stopping movement of a rack on and along said feeding line in said downstream direction to enable said analyzers to perform their respective functions, said racks each being provided with respective small magnets to permit movement of said stopped racks on and relative to said rack feeding line.

5. The container feeding system according to claim 2, wherein:
   stopper means for selectively stopping movement of a rack on and along said feeding line in said downstream direction to enable said analyzers to perform their respective functions, said racks each being provided with respective small magnets to permit movement of said stopped racks on and relative to said rack feeding line.

6. The container feeding system according to claim 3, wherein:
   stopper means for selectively stopping movement of a rack on and along said rack feeding line in said downstream direction to enable said analyzers to perform their respective functions, said racks each being provided with respective small magnets to permit movement of said stopped racks on and relative to said rack feeding line.

7. The container feeding system according to claim 2, wherein:
   respective bar code data are provided on said containers, and
   a reader is provided adjacent said sampling position for reading said bar code data and providing corresponding information for said at least one analyzer.

8. The container feeding system according to claim 3, wherein:
   respective bar code data are provided on said containers, and
   readers are provided adjacent said sampling positions for reading said bar code data and providing corresponding information to said analyzers.

9. The container feeding system according to claim 2, further comprising:
   a waiting line and an emergency line, each disposed in parallel to said rack feeding line; and
   first urging means for urging a selected rack from said rack feeding line to a selected one of said waiting line, said emergency line, and said rack recovery line, for thereby selectively moving said selected rack relative to others of said racks remaining on said rack feeding line.

10. The container feeding system according to claim 3, further comprising:
    a waiting line and an emergency line, each disposed in parallel to said rack feeding line; and
    first urging means for urging a selected rack from said rack feeding line to a selected one of said waiting line, said emergency line, and said rack recovery line, for thereby selectively moving said selected rack relative to others of said racks remaining on said rack feeding line.

11. The container feeding system according to claim 2, further comprising:
    a waiting line and an emergency line, disposed in series with respect to said rack feeding line; and
    means for urging a selected rack from said rack feeding line to a selected one of said waiting line, said emergency line, and said rack recovery line, for thereby selectively moving said selected rack relative to others of said racks remaining on said rack feeding line.

12. The container feeding system according to claim 3, further comprising:
    a waiting line and an emergency line, disposed in series with respect to said rack feeding line; and
    means for urging a selected rack from said rack feeding line to a selected one of said waiting line, said emergency line, and said rack recovery line, for thereby selectively moving said selected rack relative to others of said racks remaining on said rack feeding line.

13. The container feeding system according to claim 2, wherein:
    said rack feeding line comprises a curved portion to enable feeding of said rack therealong in a selected direction.

14. The container feeding system according to claim 3, wherein:
    said rack feeding line comprises a curved portion to enable feeding of said rack therealong in a selected direction.

15. The container feeding system according to claim 9, further comprising:
    a rack stopper operable to controllably stop further feeding of a first selected rack along said rack feeding line to thereby facilitate priority feeding of another selected rack; and
    second urging means for urging a second selected rack to said rack feeding line from one of said waiting line and said emergency line.

16. The container feeding system according to claim 10, further comprising:
    a rack stopper operable to controllably stop further feeding of a first selected rack along said rack feeding line to thereby facilitate priority feeding of another selected rack; and
    second urging means for urging a second selected rack to said rack feeding line from one of said waiting line and said emergency line.

17. The container feeding system according to claim 9, wherein:
    said at least one analyzer is provided with a corresponding central processing unit (CPU).

18. The container feeding system according to claim 10, wherein:
    said analyzers are provided with respective central processing units (CPUs).

* * * * *